US010629047B1

United States Patent
Sheu

(10) Patent No.: US 10,629,047 B1
(45) Date of Patent: Apr. 21, 2020

(54) INDOOR LOCATION BASED EMERGENCY CARE COMMUNICATION METHOD

(71) Applicant: SOUTHERN TAIWAN UNIVERSITY OF SCIENCE AND TECHNOLOGY, Tainan (TW)

(72) Inventor: Yih-Ran Sheu, Tainan (TW)

(73) Assignee: Southern Taiwan University of Science and Technology, Tainan (TW)

( * ) Notice: Subject to any disclaimer, the term of this patent is extended or adjusted under 35 U.S.C. 154(b) by 0 days.

(21) Appl. No.: 16/191,506

(22) Filed: Nov. 15, 2018

(51) Int. Cl.
| | |
|---|---|
| *G08B 25/01* | (2006.01) |
| *G08B 21/04* | (2006.01) |
| *H04W 4/02* | (2018.01) |
| *G08B 25/00* | (2006.01) |
| *G08B 21/02* | (2006.01) |
| *A61B 5/11* | (2006.01) |
| *G08B 25/10* | (2006.01) |
| *H04W 4/029* | (2018.01) |

(Continued)

(52) U.S. Cl.
CPC .......... *G08B 21/043* (2013.01); *A61B 5/1113* (2013.01); *A61B 5/1117* (2013.01); *G08B 21/02* (2013.01); *G08B 21/0272* (2013.01); *G08B 21/04* (2013.01); *G08B 21/0446* (2013.01); *G08B 25/00* (2013.01); *G08B 25/01* (2013.01); *G08B 25/016* (2013.01); *G08B 25/10* (2013.01); *H04W 4/023* (2013.01); *H04W 4/029* (2018.02); *H04W 4/33* (2018.02); *H04W 4/90* (2018.02)

(58) Field of Classification Search
CPC ...... G08B 25/00; G08B 25/01; G08B 25/016; G08B 25/10; G08B 21/02; G08B 21/0272; G08B 21/04; G08B 21/043; G08B 21/0446; A61B 5/1113; A61B 5/1117; H04W 4/02; H04W 4/023; H04W 4/029

See application file for complete search history.

(56) References Cited

U.S. PATENT DOCUMENTS

| | | | |
|---|---|---|---|
| 10,037,668 B1 * | 7/2018 | DesGarennes | G08B 21/0423 |
| 2007/0247316 A1 * | 10/2007 | Wildman | A61B 5/1113 340/572.4 |

(Continued)

FOREIGN PATENT DOCUMENTS

| | | |
|---|---|---|
| TW | M429154 U1 | 5/2012 |
| TW | 1603106 B | 10/2017 |
| TW | 1605727 B | 11/2017 |

*Primary Examiner* — Andrew W Bee
(74) *Attorney, Agent, or Firm* — Rosenberg, Klein & Lee

(57) ABSTRACT

The indoor location based emergency care communication method includes that a wearable carrier sends a start signal and an emergency care communication signal to a fixed penetrating transmission module and a fixed non-penetrating transmission module when a caretaker wearing the wearable carrier has an emergency. The fixed penetrating transmission module generates a position signal of the wearable carrier located at one of the indoor spaces and a distance signal according to a detected distance between the wearable carrier and the nearest fixed non-penetrating transmission module. A processing unit receives and analyzes the emergency care communication signal, azimuth signal and distance signal to generate a position signal to be sent to a communication device. A warning unit receives the position signal and drives the communication device to issue a warning, so that a caregiving staff can know that the caretaker needs immediate rescue.

7 Claims, 4 Drawing Sheets

(51) Int. Cl.
    *H04W 4/33* (2018.01)
    *H04W 4/90* (2018.01)

(56) References Cited

U.S. PATENT DOCUMENTS

2007/0273487 A1* 11/2007 Dawson ............... G08B 25/016
                                              340/286.07
2008/0001735 A1*  1/2008 Tran ................... G06F 19/3418
                                              340/539.22
2015/0234033 A1*  8/2015 Jamieson .................. G01S 5/04
                                              455/456.1
2019/0208363 A1*  7/2019 Shapiro ................ H04W 4/029

* cited by examiner

INDOOR LOCATION BASED EMERGENCY CARE COMMUNICATION METHOD

FIELD OF INVENTION

The present invention relates to an indoor location based emergency care communication method, in particular to the method that uses a wearable penetrating transmission module, a wearable non-penetrating transmission module, a fixed penetrating transmission module and a fixed non-penetrating transmission module to learn about a wearable carrier in an indoor space and the wearable carrier's location, so that a caregiving staff can know immediately that a care recipient has an emergency and needs immediate rescue or help, and the caregiving staff can further know about the care recipient's location at the earliest possible time to reduce the situation of misjudgment.

BACKGROUND OF INVENTION

1. Description of the Related Art

According to the progress of social changes and medical and healthcare in Taiwan, both fertility and mortality have shown a downward trend. The Ministry of the Interior of Taiwan announced in 2017 that in the statistical analysis of household registration as of Jul. 7, 2017, the proportion of the elderly population over 65 years old is accounted for 13.55%, and the young population from 0 to 14 years old is accounted for 13.22%. The number of the elderlies is nearly 80,000 more than that of the children. Up to February 2017, the difference between the two becomes increasingly larger. In addition, the whole population structure tends to become an aging structure, so that the number of people requiring long-term care is increased at the same time. Meanwhile, the function of family care declines gradually, so that the pressure of the care for individuals and families is increasing, which in turn creates many social and economic problems. Therefore, the establishment of a sound long-term caring system has become one of the key issues for Taiwan's social security system.

During a rescue process, most care recipients receive help by informing their position, wherein a global positioning system (GPS), a global navigation satellite system (GNSS) or an assisted global positioning system (AGPS) may be used in a place located in an outdoor open space to report the care recipient's location, and an indoor place relies on wireless signals for the positioning purpose.

As disclosed in R.O.C. Pat. No. I603106 entitled "Technique for determining the position of a device in a crowded indoor environment", this patent provides a positioning solution by using Wi-Fi time of flight (ToF). Once the position of the device is determined, a low-energy broadcast signal is used to confirm the position of the device which will be broadcasted to and shared with nearby devices.

As disclosed in R.O.C. Pat. No. I605727 entitled "Active radio frequency tag indoor positioning architecture and method thereof", this patent discloses a system architecture and its determination method by sending a message to a sensing node actively and estimating the current position by mutual comparisons.

As disclosed in R.O.C. Pat. No. M429154 entitled "System with both toppling detection and positioning functions", this patent discloses a toppling detection and positioning device capable of sending out a warning signal when a care recipient topples. In the meantime, the toppling position and the warning signal will be sent via a wireless sensor network comprised of a plurality of routers to a display device and an alarm of a warning device at a caregiving end. After a caregiving staff situated next to the device receives the warning signal, the caregiving staff will carry out rescue immediately.

However, in the R.O.C. Pat. No. I603106 entitled "Technique for determining the position of a device in a crowded indoor environment" as shown in FIG. 1, the start mechanism of each indoor wireless communication device 10 is turned on to learn from one of the wireless communication device 10a closer to the low-energy broadcasted signal about the position of a low-energy broadcasted signal. However, each room has partitions 20, and if the low-energy broadcasted signal is situated at the wireless communication device 10b in a room and closer to the wireless communication 10a in one of the rooms, then the warning device 30 held by the caregiving staff will receive the signal generated by the wireless communication 10a of one of the rooms, and thus will cause a misjudgment of the position where the low-energy broadcasted signal is situated.

In R.O.C. Pat. No. I605727 entitled "Active radio frequency tag indoor positioning architecture and method thereof", this patent also has the same drawback as the R.O.C. I603106 entitled "Technique for determining the position of a device in a crowded indoor environment", wherein the source of the signal is misjudged.

In R.O.C. Pat. No. M429154 entitled "System with both toppling detection and positioning functions", this patent simply uses an upper reference module and a lower reference module to detect and determine whether or not a care recipient topples, but this patent only allows a user to know in which room the care recipient topples, but cannot provide at what position of the room the care recipient topples. Therefore, the accuracy still requires further improvements.

In view of the aforementioned drawbacks of the prior art, the inventor of the present invention based on years of experience in the related industry to conduct extensive research and experiment, and finally provided a feasible solution to overcome the drawbacks of the prior art.

2. Summary of the Invention

Therefore, it is a primary objective of the present invention to overcome the drawback of the prior art which cannot provide the location of a low-power broadcasted signal correctly and thus resulting in a misjudgment when the care recipient has an emergency.

To achieve the aforementioned and other objectives, the present invention provides an indoor location based emergency care communication method comprising the steps of: generating at least an emergency care communication signal; sending one of the emergency care communication signals to at least a fixed penetrating transmission module and at least a fixed non-penetrating transmission module by a wearable penetrating transmission module and a wearable non-penetrating transmission module respectively; electrically connecting one of the wearable penetrating transmission module and wearable non-penetrating transmission module with the remaining fixed penetrating transmission module and fixed non-penetrating transmission module, and computing and converting a position signal provided for the use of emergency care; and sending the position signal to a communication device.

The aforementioned indoor location based emergency care communication method further comprises the sub-steps of: electrically connecting one of the fixed penetrating transmission modules with the remaining fixed penetrating transmission module and sensing an azimuth signal, and sensing a distance signal by the fixed non-penetrating transmission module; and analyzing the emergency care communication signal, the azimuth signal and the distance signal to generate the position signal.

The aforementioned indoor location based emergency care communication method further comprises the sub-steps of: using a distance sensing unit to detect a distance value between a wearable carrier and an environment; and using a toppling sensing unit to monitor a moving status of the wearable carrier in an arc motion path.

The aforementioned indoor location based emergency care communication method further comprises the sub-steps of: defining a distance setting and a motion change setting range, and the motion change setting range being one that restores calmness after the moving status has gone through a severe motion; and generating a start signal if the distance value is smaller than the distance setting and the moving status complies with the motion change setting range.

The aforementioned indoor location based emergency care communication method further comprises the sub-step of: receiving the position signal by a warning unit to issue a warning.

The aforementioned indoor location based emergency care communication method further comprises the sub-steps of: defining a press button to detect the emergency care communication signal, and send out the emergency care communication signal for analysis.

In summation of the description above, the present invention obviously has the following advantages and effects:

1. If the care recipient wearing the wearable carrier of the present invention has an emergency, the analysis module will sense and generate the start signal and the emergency care communication signal, and the wearable penetrating transmission module and wearable non-penetrating transmission module will send the start signal and the emergency care communication signal to the fixed penetrating transmission module and fixed non-penetrating transmission module, and then the fixed penetrating transmission module will sense one another to generate an azimuth signal of the wearable carrier situated in an indoor space, and one of the fixed non-penetrating transmission modules senses the distance from the wearable carrier to generate the distance signal, and the processing unit receives and analyzes the aforementioned signal to generate the position signal and then sends the position signal to communication device, and the warning unit receives the position signal to issue a warning, so that the caregiving staff can know from the communication device immediately that the care recipient has an emergency and needs immediate help. Therefore, the caregiving staff can know the care recipient's location at the earliest possible time to reduce the situation of misjudgment.

2. If the care recipient needs help, the care recipient may press the press button of the present invention to let the caregiving staff know about the care recipient's location and go for rescue.

DESCRIPTION OF THE PREFERRED EMBODIMENTS

To make it easier for our examiner to understand the objective, technical characteristics, structure, innovative features, and performance of the invention, we use preferred embodiments together with the attached drawings for the detailed description of the invention. It is noteworthy that the embodiments are provided for the purpose of illustrating the invention but not intended for limiting the scope of the invention.

Figure 1:
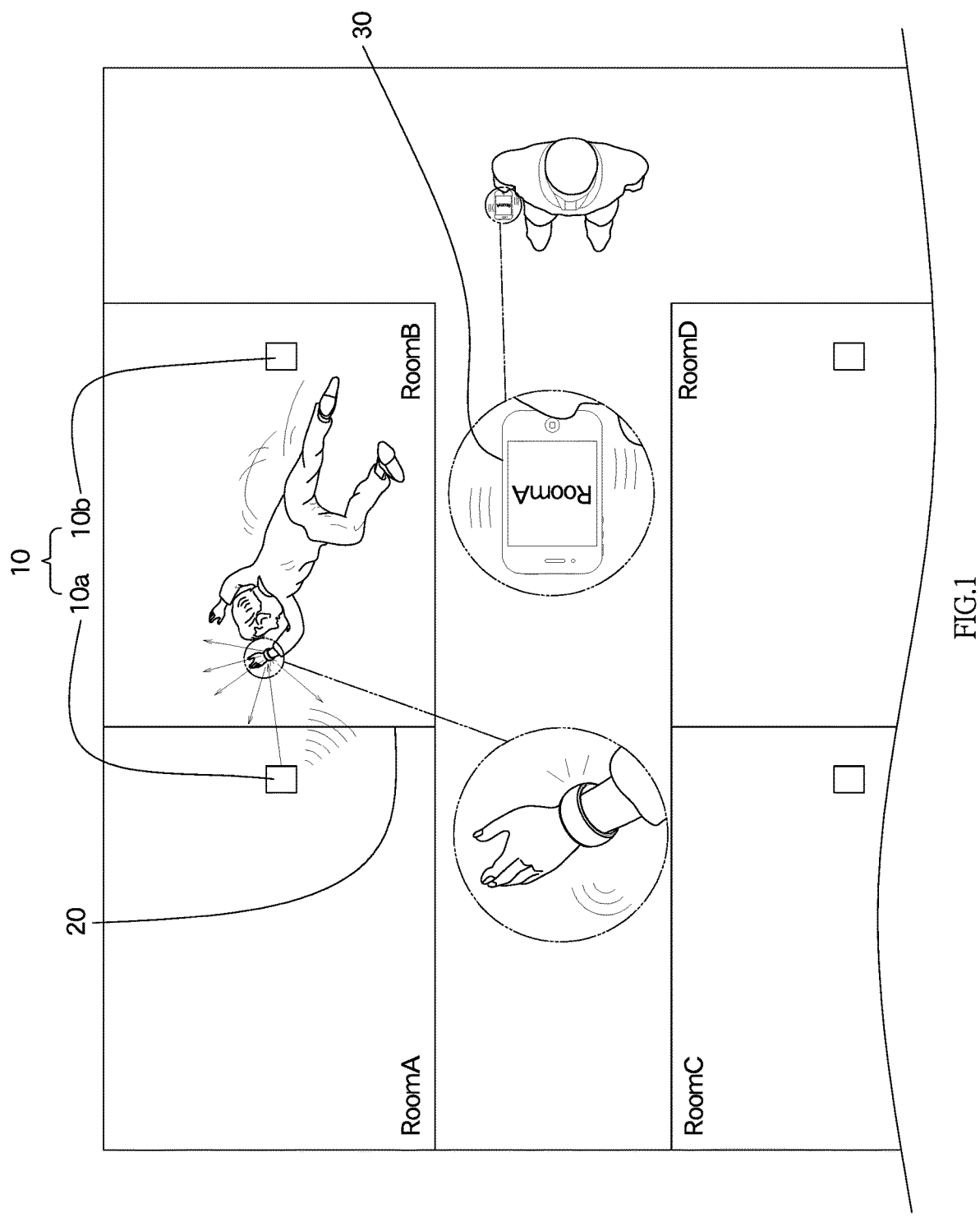
FIG. 1 is a schematic view showing the using status of a prior art.
Figure 2:
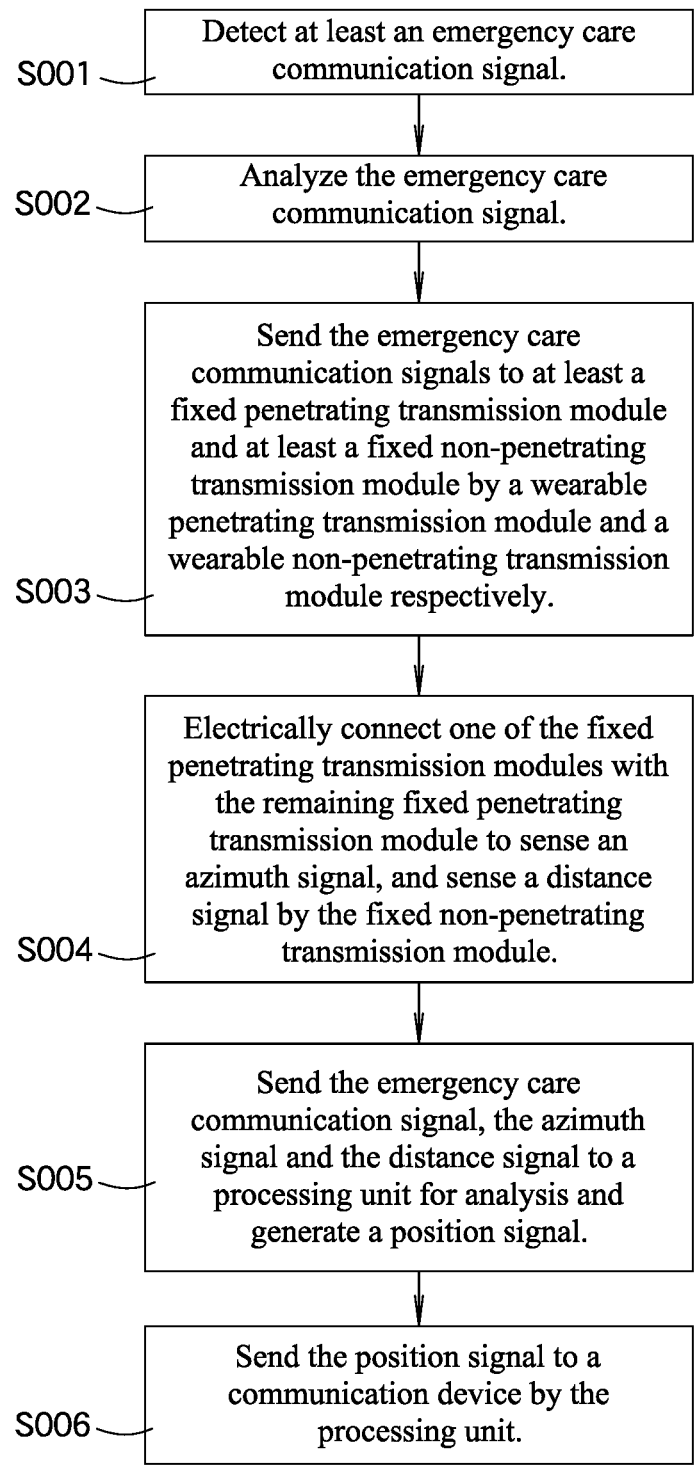
FIG. 2 is a flow chart showing the procedure of the present invention.
Figure 3:
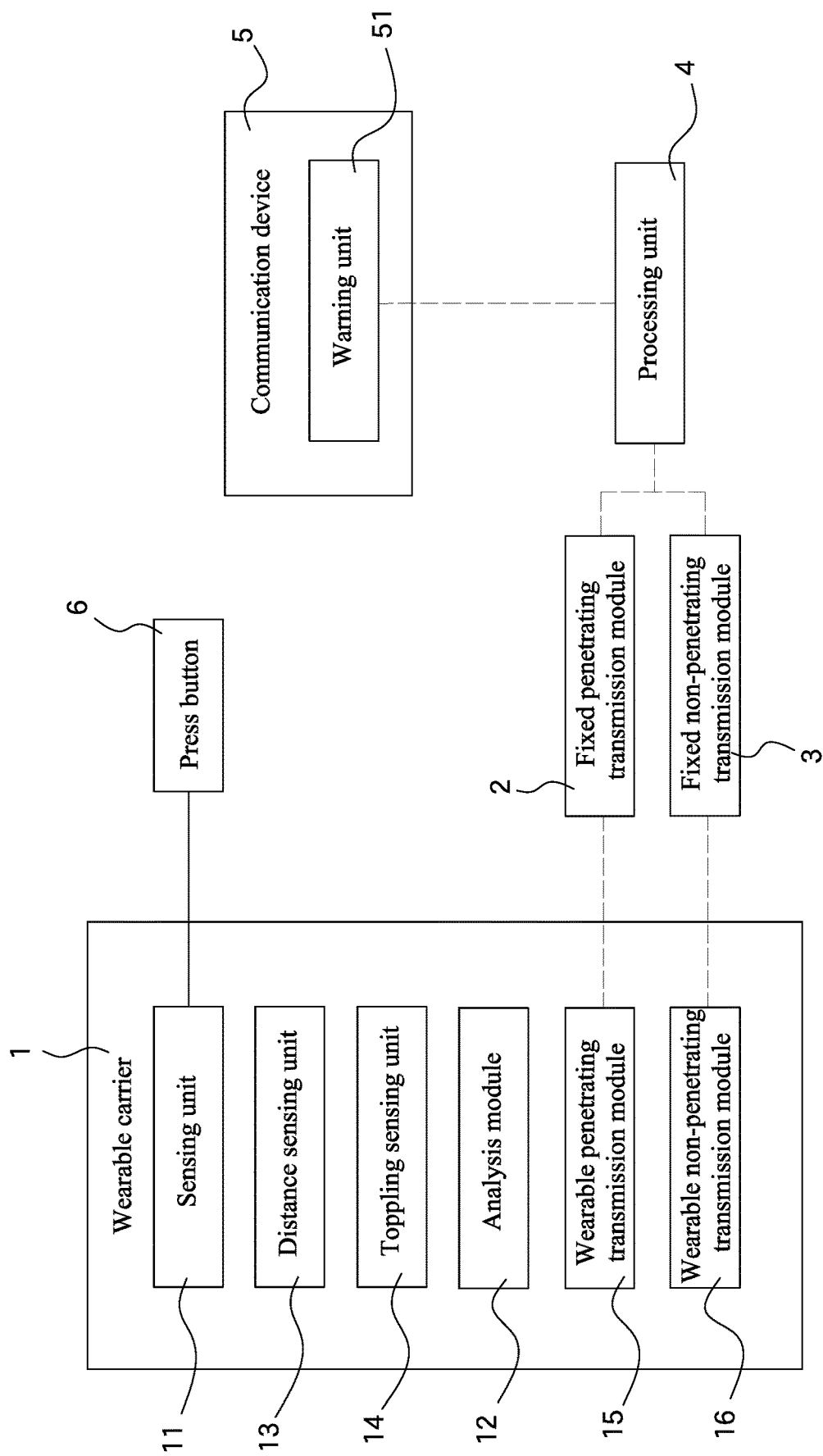
FIG. 3 is a block diagram of the structure of the present invention.

With reference to FIGS. 2 and 3 for an indoor location based emergency care communication method of the present invention, the indoor location based emergency care communication method comprises the following steps (S001 to S006):

S001: Detect at least an emergency care communication signal.

S002: Analyze the emergency care communication signal.

In a specific embodiment, the present invention uses a wearable carrier 1 to detect and analyze the emergency care communication signal, and the wearable carrier 1 has a sensing unit 11 and an analysis module 12, and the sensing unit 11 is electrically coupled to the analysis module 12, and the sensing unit 11 senses an emergency care communication signal and sends the emergency care communication signal to the analysis module 12 for analysis.

In an exemplary embodiment, the wearable carrier 1 further has a distance sensing unit 13 and a toppling sensing unit 14, and the distance sensing unit 13 detects a distance value between the wearable carrier 1 and an environment, and the toppling sensing unit 14 monitors a moving status of the wearable carrier 1 in an arc motion path. In a preferred embodiment, the analysis module 12 is coupled to the distance sensing unit 13 and the toppling sensing unit 14, and the analysis module 12 has a distance setting and a motion change setting range, and the motion change setting range restore calmness after the moving status has gone through a severe motion. If the distance value is smaller than the distance setting and the moving status complies with the motion change setting range, then the analysis module 12 will generate a start signal.

S003: Send the emergency care communication signals to at least a fixed penetrating transmission module 2 and at least a fixed non-penetrating transmission module 3 by a wearable penetrating transmission module 15 and a wearable non-penetrating transmission module 16 respectively. In a preferred embodiment, the wearable non-penetrating transmission module 16 and/or the fixed non-penetrating transmission module 3 are infrared distance sensing modules or laser modules which are optical communication modules unable to penetrate through an obstacle (such as a wall) for signal transmission, and the wearable penetrating transmission module 15 and/or the fixed penetrating transmission module 2 are signal transmission module of a wireless communication technology (such as Bluetooth, WIFI, RFID, RF wireless communication or radar) capable of penetrating an obstacle easily).

S004: Electrically connect one of the fixed penetrating transmission modules 2 with the remaining fixed penetrating transmission module 2a to sense an azimuth signal, and sense a distance signal by the fixed non-penetrating transmission module 3.

In a specific embodiment, the wearable penetrating transmission module 15 is installed at the wearable carrier 1 and electrically coupled to the analysis module 12, and the analysis module 12 sends the emergency care communication signal to the wearable penetrating transmission module 15. Since the fixed penetrating transmission module 2 is electrically coupled to the wearable penetrating transmission module 15, therefore the wearable penetrating transmission module 15 can send the emergency care communication signal to the fixed penetrating transmission module 2. In a preferred embodiment of the present invention, the fixed penetrating transmission module 2 is installed at each indoor space (such as a living room, kitchen, room or bathroom), so that when one of the fixed penetrating transmission modules 2 receives the emergency care communication signal, the fixed penetrating transmission modules 2 sense each other, and one of the fixed penetrating transmission modules 2 closer to the wearable carrier 1 sends out the azimuth signal.

In addition, the wearable non-penetrating transmission module 16 is installed at the wearable carrier 1 and electrically coupled to the analysis module 12 and the fixed non-penetrating transmission module 3, and the analysis module 12 sends the emergency care communication signal to the wearable non-penetrating transmission module 16, and the wearable non-penetrating transmission module 16 sends the emergency care communication signal to one of the fixed non-penetrating transmission modules 3. In an exemplary embodiment, the fixed non-penetrating transmission module 3 is installed at each indoor space. In another preferred embodiment of the present invention, the wearable non-penetrating transmission module 16 and the fixed non-penetrating transmission module 3 are infrared distance sensing modules or laser modules which are optical communication modules blocked by an obstacle (such as a wall) easily. Since the transmission of infrared and laser signals cannot penetrate the wall easily, therefore the emergency care communication signal generated by the wearable carrier 1 will be sent to one of the fixed non-penetrating transmission modules 3 by the wearable non-penetrating transmission module 16 situated in the indoor space, and then one of the fixed non-penetrating transmission modules 3 will sense its distance from the wearable carrier 1 to generate a distance signal of a certain position of the indoor space.

S005: Send the emergency care communication signal, the azimuth signal and the distance signal to a processing unit 4 for analysis and generate a position signal.

In a specific embodiment, the processing unit 4 is electrically coupled to the fixed penetrating transmission module 2 and the fixed non-penetrating transmission module 3, and the processing unit 4 receives the emergency care communication signal, the azimuth signal of the fixed penetrating transmission module 2, and the distance signal of one of the fixed non-penetrating transmission modules 3, and then analyzes these signals to generate the position signal.

S006: Send the position signal to a communication device 5 by the processing unit 4.

In a specific embodiment, the communication device 5 is electrically coupled to the processing unit 4, and the processing unit 4 sends the position signal to the communication device 5. In an exemplary embodiment, the communication device 5 is further coupled to a warning unit 51, and the warning unit 51 and the processing unit 4 are electrically coupled to each other, and the position signal is received to issue a warning. In another exemplary embodiment, the warning unit 51 sends out the warning signal by broadcasting, short messages, emails, pushes, etc. through a transmission interface such as handheld mobile communication, WIFI, Bluetooth, etc.

Figure 4:
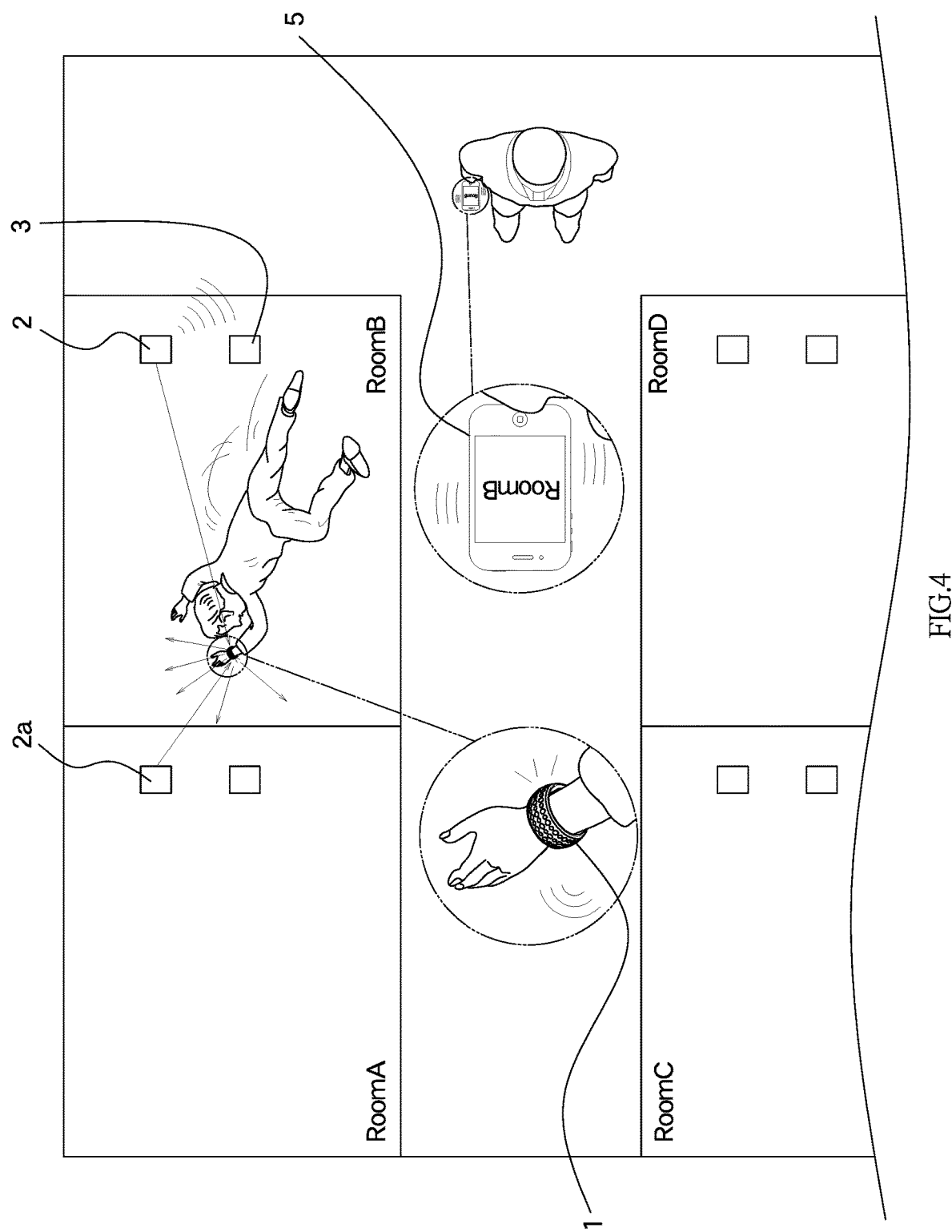
FIG. 4 is a schematic view showing the using status of the present invention.

In FIGS. 3 and 4, if a care recipient wearing the wearable carrier 1 has an accident (such as a topple), the distance value sensed by the analysis module 12 is smaller than the distance setting, and the moving status complies with the motion change setting range, then the analysis module 12 will generate the start signal, and the sensing unit 11 will sense the emergency care communication signal (such as the care recipient's heartbeat), and the start signal and the emergency care communication signal will be sent to the analysis module 12, and the analysis module 12 will send the emergency care communication signal through the wearable penetrating transmission module 15 and the wearable non-penetrating transmission module 16 to the fixed penetrating transmission module 2 and the fixed non-penetrating transmission module 3 respectively, and then one of the fixed penetrating transmission modules 2 and the remaining fixed penetrating transmission module 2a sense each other to generate an azimuth signal of the wearable carrier 1 situated in one of the indoor spaces, and one of the fixed non-penetrating transmission modules 3 senses its distance from the wearable carrier 1 to generate the distance signal, and then the emergency care communication signal, the azimuth signal and the distance signal will be sent to the processing unit 4 for analysis to generate a position signal, and the position signal will be sent to the communication device 5. The warning unit 51 receives the position signal to let the communication device 5 issue a warning, so that a caregiving staff can know immediately from the communication device 5 (such as a mobile phone) that the care recipient has an emergency and needs immediate help. This arrangement allows the caregiving staff to know the care recipient's location at the earliest possible time, so as to reduce the situation of misjudgment.

In addition, the wearable carrier 1 further has a press button 6 coupled to the sensing unit 11. When the care recipient needs help and presses the press button 6, the sensing unit 11 will sense the emergency care communication signal of the care recipient and send the emergency care communication signal to the analysis module 12 for analysis. Embodiments other than this embodiment are substantially the same as the first embodiment, and thus will not be repeated.

What is claimed is:

1. An indoor location based emergency care communication method for an indoor location having a plurality of rooms, comprising:

establishing a plurality of fixed penetrating transmission modules in respective rooms of the location and a plurality of fixed non-penetrating transmission modules in respective rooms of the location;

establishing a wearable carrier device to be worn on a care recipient, the wearable carrier device including a wearable penetrating transmission module and a wearable non-penetrating transmission module;

generating at least an emergency care communication signal; sending the emergency care communication signal to at least a first of the fixed penetrating transmission modules and at least a first of the fixed non-penetrating transmission modules disposed in a first of the rooms by actuating the wearable penetrating transmission module and the wearable non-penetrating transmission module respectively of the wearable carrier device disposed in the first room;

establishing communication between one of the wearable penetrating and wearable non-penetrating transmission modules and a second of the fixed penetrating or fixed non-penetrating transmission modules, and computing a position signal indicating a position of the wearable carrier device worn by the care recipient within the indoor location for aiding emergency care response to the care recipient; and sending the position signal to a communication device.

2. The indoor location based emergency care communication method of claim 1, further comprising:

establishing communication between the first fixed penetrating transmission module and the second fixed penetrating transmission module, and generating an azimuth signal for the location of the wearable carrier device worn by the care recipient;

sensing a distance signal for the location of the wearable carrier worn by the care recipient with respect to one of the first and second fixed non-penetrating transmission modules; and analyzing the emergency care communication signal, the azimuth signal, and the distance signal to generate the position signal.

3. The indoor location based emergency care communication method of claim 2, further comprising:

using a distance sensing unit to sense a distance value between the wearable carrier device and a reference disposed in a surrounding environment; and using a toppling sensing unit to monitor a moving status of the wearable carrier with respect to a predetermined arc motion path.

4. The indoor location based emergency care communication method of claim 3, further comprising:

predefining a distance setting and a motion change setting range, the motion change setting range indicating a settling of the moving status after undergoing a severe motion; and generating a start signal if the distance value is smaller than the distance setting and the moving state is within the motion change setting range.

5. The indoor location based emergency care communication method of claim 4, further comprising:

receiving the position signal by a warning unit to issue a warning.

6. The indoor location based emergency care communication method of claim 1, further comprising:

defining a press button on the wearable carrier device to detect the emergency care communication signal, and send out the emergency care communication signal for analysis.

7. The indoor location based emergency care communication method of claim 1, wherein the second fixed penetrating transmission module is disposed in a second room.

* * * * *